United States Patent
Ulrici et al.

(10) Patent No.: US 12,263,023 B2
(45) Date of Patent: Apr. 1, 2025

(54) 3D X-RAY DEVICE AND METHOD FOR PRODUCING A 3D X-RAY IMAGE

(71) Applicant: DENTSPLY SIRONA Inc., York, PA (US)

(72) Inventors: Johannes Ulrici, Darmstadt (DE); Kai Stannigel, Weinheim (DE); Wolf Blecher, Hemsbach (DE)

(73) Assignee: Dentsply Sirona Inc., York, PA (US)

( * ) Notice: Subject to any disclaimer, the term of this patent is extended or adjusted under 35 U.S.C. 154(b) by 358 days.

(21) Appl. No.: 17/780,107

(22) PCT Filed: Nov. 27, 2020

(86) PCT No.: PCT/EP2020/083700
§ 371 (c)(1),
(2) Date: May 26, 2022

(87) PCT Pub. No.: WO2021/105402
PCT Pub. Date: Jun. 3, 2021

(65) Prior Publication Data
US 2023/0009790 A1    Jan. 12, 2023

(30) Foreign Application Priority Data
Nov. 29, 2019 (EP) .................................. 19212720

(51) Int. Cl.
*A61B 6/03* (2006.01)
*A61B 6/00* (2024.01)
(Continued)

(52) U.S. Cl.
CPC ................ *A61B 6/032* (2013.01); *A61B 6/06* (2013.01); *A61B 6/4021* (2013.01);
(Continued)

(58) Field of Classification Search
CPC ........... A61B 6/027; A61B 6/032; A61B 6/06; A61B 6/107; A61B 6/4021; A61B 6/4035;
(Continued)

(56) References Cited

U.S. PATENT DOCUMENTS 8,238,522 B2   8/2012 Frey
2003/0147502 A1   8/2003 Heismann
(Continued)

FOREIGN PATENT DOCUMENTS

EP    2234541       10/2010
EP    2234541 B1    5/2016
(Continued)

OTHER PUBLICATIONS

International Search Report; PCT/EP2020/083700; Feb. 9, 2021 (completed); Feb. 19, 2021 (mailed).
(Continued)

*Primary Examiner* — Mark R Gaworecki
(74) *Attorney, Agent, or Firm* — SCHWEGMAN LUNDBERG & WOESSNER, P.A.

(57) ABSTRACT

A 3D X-ray device including an X-ray detector, an X-ray source and a computer. The X-ray detector and the X-ray source are moved about an object volume to be recorded on movement paths with a rotation of at least 185°. A number of X-ray projection images are recorded from different directions. X-rays irradiate the object volume in one of the irradiation directions and are captured by the detector. A 3D X-ray image of the object volume is calculated from the recorded X-ray projection images by a reconstruction method. The X-ray detector is arranged asymmetrically relative to a central axis through a center of rotation of the 3D X-ray device. A first fan beam and an opposite second fan beam rotated 180° form an overlap region. At least one
(Continued)

X-ray filter is placed between the X-ray source and the object volume for attenuating an X-ray dose inside the overlap region.

13 Claims, 7 Drawing Sheets

(51) Int. Cl.
*A61B 6/06* (2006.01)
*A61B 6/40* (2024.01)
*G21K 1/10* (2006.01)
*A61B 6/02* (2006.01)
*A61B 6/10* (2006.01)
*A61B 6/50* (2024.01)

(52) U.S. Cl.
CPC .............. *A61B 6/4441* (2013.01); *G21K 1/10* (2013.01); *A61B 6/027* (2013.01); *A61B 6/107* (2013.01); *A61B 6/4035* (2013.01); *A61B 6/4078* (2013.01); *A61B 6/501* (2013.01)

(58) Field of Classification Search
CPC ..... A61B 6/4078; A61B 6/4441; A61B 6/501; A61B 6/51; G21K 1/10
See application file for complete search history.

(56) References Cited

U.S. PATENT DOCUMENTS

| | | |
|---|---|---|
| 2004/0258195 A1 | 12/2004 | Hara |
| 2005/0089146 A1 | 4/2005 | Toth |
| 2007/0172104 A1 | 7/2007 | Nishide |
| 2010/0308229 A1 | 12/2010 | Bertram |
| 2011/0261923 A1 | 10/2011 | Schmitt |
| 2014/0270069 A1 | 9/2014 | Ganguly |

FOREIGN PATENT DOCUMENTS

| | | |
|---|---|---|
| EP | 3827750 | 6/2021 |
| JP | 2009089810 A | 4/2009 |
| JP | 2011502679 A | 1/2011 |
| JP | 2012515592 A | 7/2012 |
| JP | 2018536487 A | 12/2018 |
| WO | 2021105402 | 6/2021 |

OTHER PUBLICATIONS

International Preliminary Report on Patentability; PCT/EP2020/083700; Feb. 9, 2021 (completed); Feb. 19, 2021 (mailed).
Written Opinion of the International Searching Authority; PCT/EP2020/083700; Feb. 9, 2021 (completed); Feb. 19, 2021 (mailed).
Japanese Office Action dated Jul. 11, 2024.
"European Application Serial No. 19212720.7, Extended European Search Report mailed Apr. 23, 2020", 8 pgs.
"European Application Serial No. 19212720.7, Response filed Dec. 2, 21 to Extended European Search Report mailed Apr. 23, 2020", 34 pgs.

3D X-RAY DEVICE AND METHOD FOR PRODUCING A 3D X-RAY IMAGE

CROSS-REFERENCE TO RELATED APPLICATIONS

This is a National Phase application of International Application No. PCT/EP2020/083700, filed Nov. 27, 2020, which claims the benefit of and priority to European Application Ser. No. 19212720.7, filed on Nov. 29, 2019, which are herein incorporated by reference for all purposes.

TECHNICAL FIELD

The invention relates to a 3D X-ray device comprising an X-ray detector, an X-ray source and a computer, wherein the X-ray detector and the X-ray source are moved about an object volume to be recorded on a movement path with a rotation of at least 185°, wherein a plurality of X-ray projection images are recorded from different irradiation directions, whereby X-rays, which are produced by means of the X-ray source, irradiate the object volume in one of the irradiation directions and are captured by the X-ray detector, wherein a 3D X-ray image of the object volume is calculated from the recorded X-ray projection images by means of a reconstruction method.

BACKGROUND OF THE INVENTION

A number of 3D X-ray devices and measurement methods are known from the state of the art.

U.S. Pat. No. 8,238,522 B2 discloses a filter changing assembly which can be used in an X-ray device, for example, and comprises shape filters which can be used to produce a radiation beam and which can, for example, be moved back and forth. The filter changing assembly also includes beam hardening filters which can be used to change the energy spectrum of the radiation beam and which can also be moved back and forth, for example. The filter changing assembly includes a control system which can be used to select at least one of the filters and move the selected filter.

US 2014/0270069 A1 discloses an X-ray device comprising an X-ray source, a collimator for modifying the X-rays, and a motorized system that can be operated to control the collimator. The leaves of the collimator can be configured to modulate a beam quality of the X-rays. The individual leaves of the collimator can be made of different metals, such as aluminum, copper or tin, for example, and have different thicknesses, so that the radiation absorption can be influenced as desired.

US 2007/0172104 A1 discloses a CT device with an X-ray filter for improving the image quality of a 3D X-ray image. The X-ray filter serves to reduce the dose of the irradiated object.

One disadvantage of the mentioned methods is that, in the case of a rotation of more than 180°, the X-ray device irradiates an overlap region twice, so that objects inside the overlap region are irradiated with a higher dose.

The object of the present invention is therefore to provide a method and a 3D X-ray device, which records a 3D X-ray image with a homogeneous dose that is distributed across the object volume.

SUMMARY OF THE INVENTION

The invention relates to a 3D X-ray device comprising an X-ray detector, an X-ray source and a computer, wherein the X-ray detector and the X-ray source are moved about an object volume to be recorded on a movement path with a rotation of at least 185°. A plurality of X-ray projection images are recorded from different irradiation directions, whereby X-rays, which are produced by means of the X-ray source, irradiate the object volume in one of the irradiation directions and are captured by the X-ray detector. A 3D X-ray image of the object volume is subsequently calculated from the recorded X-ray projection images by means of a reconstruction method. The X-ray detector is arranged asymmetrically relative to a central axis through a center of rotation of the 3D X-ray device, wherein a first fan beam and an opposite second fan beam rotated 180° form an overlap region. At least one X-ray filter is disposed between the X-ray source and the object volume for attenuating an X-ray dose inside the overlap region, wherein no X-ray filter for attenuating the X-ray dose or a second X-ray filter having a width that differs from a width of the X-ray filter disposed inside the overlap region is provided in the regions of the two fan beams outside the overlap region.

The 3D X-ray device can be a CT device or a DVT device, for example, wherein the two-dimensional X-ray projection images are produced from the different irradiation directions. During a rotation, the X-ray detector and the X-ray source are rotated at least 185° around the object volume. During rotation, the X-ray detector and the X-ray source describe a, for example, circular or elliptical movement about the object volume, so that the center of rotation of the 3D X-ray device is defined by the circular movement. The central axis of the 3D X-ray device extends from the X-ray source through the center of rotation. The X-ray detector is arranged asymmetrically relative to this central axis, so that, for example, a first distance from the central axis to a first edge of the X-ray detector is smaller than a second distance from the central axis to a second edge of the X-ray detector. The 3D X-ray device can comprise an aperture which is controlled such that the fan beam irradiates the entire sensor surface of the X-ray detector, so that the fan beam, too, is arranged asymmetrically relative to the central axis. For any given first fan beam from a certain irradiation direction there is therefore an opposite second fan beam that is rotated 180°, whereby the first fan beam and the second fan beam are arranged asymmetrically to the central axis. Inside the overlap region, both the first fan beam and the second fan beam irradiate the object volume. The X-ray filter is thus shaped and disposed inside the overlap region such that the attenuation of the X-ray dose inside the overlap region results in a distribution of the dose inside the entire object volume that is as homogeneous as possible. One advantage of the 3D X-ray device is therefore that the arrangement of the asymmetrical X-ray detector and the selection and arrangement of the X-ray filter inside the overlap region make it possible to achieve a dose distribution inside the entire object volume that is as homogeneous as possible. The dose burden for the patient is thus reduced.

No X-ray filter for attenuating the X-ray dose is therefore disposed in the regions of the object volume outside the overlap region, because said regions are irradiated only once, and not twice as is the case in the overlap region. It is also possible to dispose an additional X-ray filter having a constant or variable width and constant or variable attenuation in these regions outside the overlap region, whereby the X-ray filter is appropriately shaped and disposed inside the overlap region to attenuate the dose inside the overlap region to a dose value within the values outside the overlap region, so that the dose progression inside the object volume is as homogeneous as possible.

The 3D X-ray device can advantageously be a CT device or a DVT device.

The 3D X-ray device can therefore be a conventional computed tomography (CT) device or a conventional digital volume tomography (DVT) device, so that the inventive 3D X-ray device can be produced from a conventional CT device or DVT device without much technical effort by equipping said device with the described X-ray filter.

The shape of the X-ray filter can advantageously be selected such that a transmission curve of the X-ray filter decreases or increases monotonically across the overlap region.

This shape of the X-ray filter consequently makes the desired dose reduction in the overlap region possible.

The shape of the X-ray filter can advantageously be selected such that a transmission curve of the X-ray filter is point-symmetrical relative to the center of rotation and has a 50% attenuation of the X-ray dose at a center point of the overlap region.

In particular in the case of a beam lobe with a spatially constant or approximately constant intensity, this configuration ensures a dose distribution in the object volume that is as homogeneous as possible.

The transmission curve of the X-ray filter is a function of the transmission or attenuation of the X-ray radiation in dependence on an x-coordinate along the entire length of the X-ray filter. The X-ray filter is therefore shaped and disposed relative to the fan beam such that the transmission curve is point-symmetrical relative to the center of rotation and has a 50% attenuation of the X-ray dose at a center point of the overlap region.

The center point of the overlap region is the projection of the center of rotation onto the X-ray detector.

The dose of the first fan beam and the dose of the second opposite fan beam are thus summed, so that the total of the dose results in a homogeneous dose progression inside the overlap region.

The shape of the X-ray filter can advantageously be selected such that a transmission curve of the X-ray filter increases monotonically inside the overlap region, for example from 0% to 100%.

The shape of the X-ray filter can advantageously be a cuboid shape, a wedge shape, a stepped shape or a shape adapted to a weighting curve of a 3D reconstruction method.

The X-ray filter can thus have a cuboid shape, for example, whereby the transmission curve has a constant attenuation of the X-ray dose of 50% along the entire length of the overlap region. In the case of a wedge shape of the X-ray filter, the width of the X-ray filter along the length is selected such that the transmission curve, for example, creates a straight line from 0% to 100% of the transmission along the length of the X-ray filter. In the case of a stepped shape of the X-ray filter, the width of the X-ray filter along the entire length is selected such that the transmission curve has a stepped progression. The transmission curve can have uniform stepped increases, for example, that are arranged point-symmetrically to the center of the overlap region. The shape of the X-ray filter can be adapted to the weighting curve of a 3D reconstruction method, whereby the width of the X-ray filter along the length is selected such that a point-symmetrical transmission curve having a selected progression is produced.

The X-ray detector and the X-ray source can advantageously be moved about the object volume to be recorded on a movement path with a rotation of at least 360°.

As a result of the rotation of at least 360°, the entire object volume to be recorded is measured twice, so that for any given first radiation beam there is a second opposite radiation beam, and a homogeneous dose progression inside the overlap region is created.

To attenuate the X-ray dose inside the overlap region, a plurality of X-ray filters of different widths and shapes can advantageously be disposed between the X-ray source and the object volume.

The individual X-ray filters can be two wedge-shaped X-ray filters and a cuboid X-ray filter, for example, that are disposed inside the overlap region one above the other in the direction of the X-rays. The X-ray filters disposed one above the other thus also produce the desired transmission curve.

At the transition between the overlap region and the remaining region of the first fan beam and the second opposite fan beam, it is important that no intermittency of the dose progression develops.

The X-ray filter can advantageously be constructed of a plurality of layers, wherein the individual layers consist of materials having different X-ray absorption properties, whereby the individual layers of the X-ray filter are constructed such that a desired transmission curve is produced.

The X-ray filter is thus constructed from a plurality of layers of different materials, such as copper or aluminum, so that the desired, possibly point-symmetrical, transmission curve is produced. The individual layers of the X-ray filter can be arranged parallel to the X-rays of the X-ray fan beam, so that the different X-ray absorption properties of the materials and the width of the individual layers produce the desired transmission curve.

The 3D X-ray device can advantageously comprise an aperture between the X-ray source and the object volume in order to form the fan beam, whereby the X-ray filter is disposed between the aperture and the X-ray source or between the aperture and the object volume.

The fan beam is therefore collimated by the aperture, whereby the X-rays hitting the aperture are absorbed. The X-ray filter can thus be disposed in front of the aperture or behind the aperture.

The computer can advantageously be configured such that the attenuation of the X-ray dose by the at least one X-ray filter is taken into account in the calculation of the 3D X-ray image by means of the reconstruction method.

The attenuation or the transmission curve of the X-ray filter is thus taken into account in the calculation of the 3D X-ray image, so that potential distortions and imaging errors are prevented. The calculation by means of the reconstruction method therefore assumes the correct, X-ray filter-attenuated dose for each voxel of the object volume.

The X-ray filter can advantageously be made of copper or aluminum.

The materials copper and aluminum are particularly advantageous for the targeted attenuation of X-rays.

The X-ray filter can advantageously be moved automatically into a desired position relative to the radiation beam by means of a control unit and a drive unit.

The drive unit can comprise an electric motor, for example, so that the X-ray filter is positioned as desired relative to the radiation beam under the control of the control unit. This may be necessary, for example, if the size of the fan beam is changed by an adjustment of the aperture. The X-ray filter is therefore positioned relative to the radiation beam in the desired manner, for example such that the transmission curve is point-symmetrical and has a 50% attenuation of the X-ray dose at the center point of the overlap region.

The invention further relates to a method for producing a 3D X-ray image by means of the 3D X-ray device according to the inventive method discussed above, whereby the attenuation of the X-ray dose by the X-ray filter is taken into account in the calculation of the 3D X-ray image from the individual X-ray projection images by means of the reconstruction method.

One advantage of the inventive method is therefore that, using the above-described 3D X-ray device with the described X-ray filter, a 3D X-ray image is recorded with a reduced dose burden. The calculation by means of the reconstruction method therefore assumes the X-ray filter-attenuated dose for each voxel of the object volume.

BRIEF DESCRIPTION OF THE DRAWINGS

The invention will be explained with reference to the drawings. The drawings show.

DETAILED DESCRIPTION OF THE INVENTION

Figure 1:
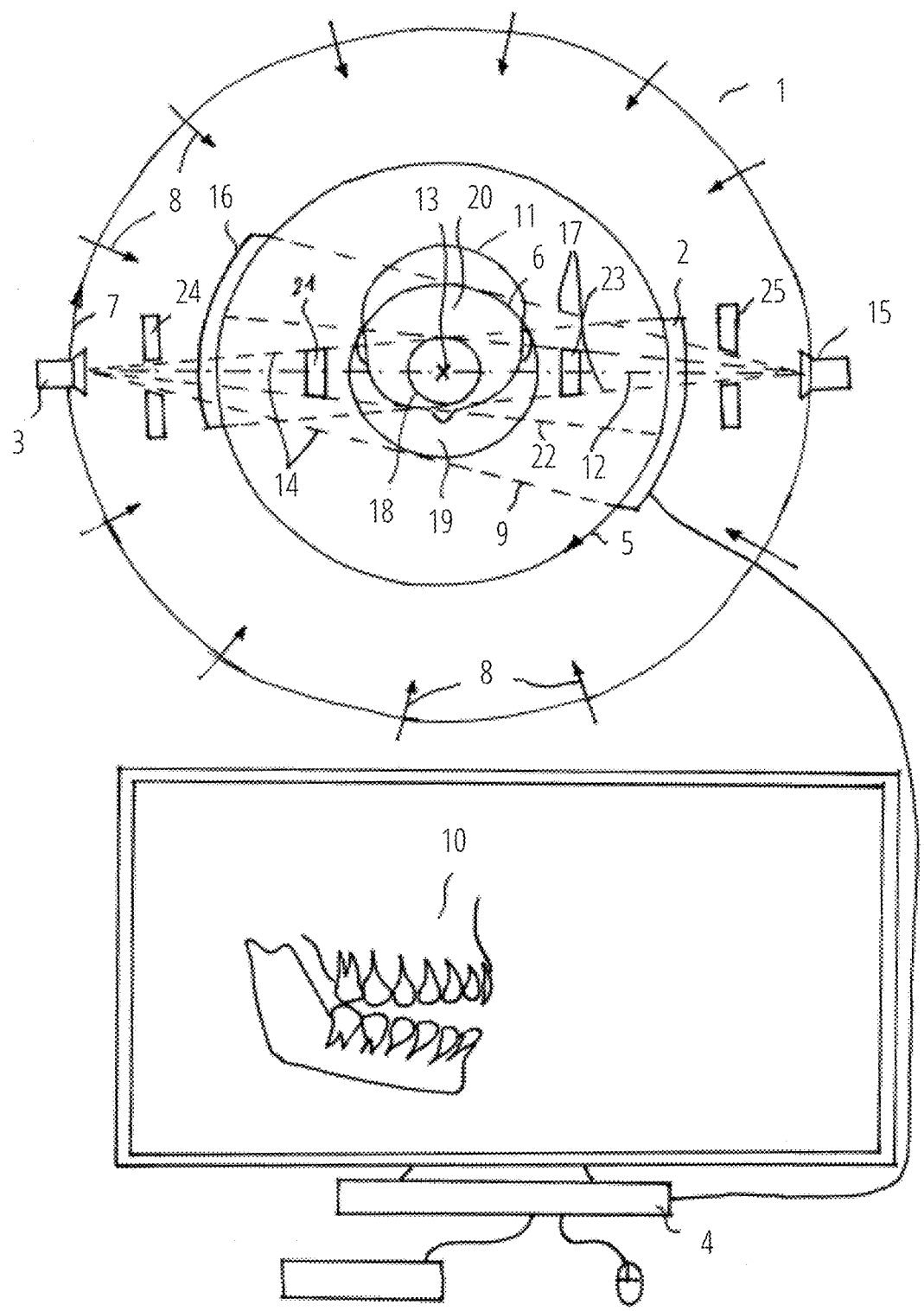
FIG. 1 a sketch of a 3D X-ray device,
FIG. 2 a rectangular embodiment of the X-ray filter,
FIG. 3 a wedge-shaped embodiment of the X-ray filter,
FIG. 4 a stepped embodiment of the X-ray filter,
FIG. 5 a wedge-shaped embodiment of the X-ray filter,
FIG. 6 a stepped embodiment of the X-ray filter consisting of two pieces,
FIG. 7 a wedge-shaped embodiment of the X-ray filter consisting of three layers.

FIG. 1 shows a sketch of a 3D X-ray device 1 comprising an X-ray detector 2, an X-ray source 3 and a computer 4. The X-ray detector 2 is moved clockwise about an object volume 6 to be recorded on a first movement path 5 with a rotation of at least 360°, while the X-ray source 3 is moved in a corresponding manner about an object volume 6 to be recorded on a second movement path 7 with a rotation of at least 360°. During the rotation, a plurality of X-ray projection images are recorded from different irradiation directions 8, whereby X-rays 9, which have been produced by means of an X-ray source 3, irradiate the object volume 6 in the corresponding irradiation direction 8 and are captured by the X-ray detector 2. A 3D X-ray image 10 of a patient 11 positioned in the object volume 6 is subsequently calculated from the recorded X-ray projection images of the different irradiation directions by means of a reconstruction method and using the computer 4. The X-ray detector 2 is arranged asymmetrically relative to a central axis 12 of the 3D X-ray device 1 through a center of rotation 13. A first fan beam 14 of the X-rays 9 irradiates the object volume 6. The X-ray source 3 is rotated 180° along the movement path 7 in order to reach an opposite position 15. The X-ray detector 2 is likewise correspondingly rotated 180° in order to reach an opposite position 16 of the X-ray detector 2. In the opposite position 15, the X-ray source emits a second, opposite fan beam 17, which irradiates the object volume 6. The first fan beam 14 and the second fan beam 17 irradiate a common overlap region 18. This overlap region 18 is thus measured and irradiated twice, whereas a first remaining region 19 of the first fan beam 14 and a second remaining region 20 of the second fan beam 17 inside the object volume 6 are irradiated and recorded only once. For every first fan beam 14 of one of the irradiation directions 8, there is therefore an opposite second fan beam 17 and an overlap region 18. Overlaying all of the overlap regions 18 of the different irradiation directions creates a cylindrical volume of the overlap region 18, which in plan view is shown as a circle around the center of rotation 13. Overlaying all of the fan beams 14, 17 of the different irradiation directions 8 likewise results in a cylindrical volume of the object volume 6, which is shown in plan view as a circle. During the movement of the X-ray detector 2 about the object volume 6, 30 to 1,000 X-ray projection images can be recorded per seconds in angular increments between 0.01° and 10°, for example.

To attenuate the X-ray dose inside the overlap region 18, an X-ray filter 21 is disposed in a fixed position relative to the X-ray source 3 and thus relative to the first fan beam 14. The X-ray dose inside the overlap region 18 is consequently attenuated as a part of the first fan beam 14, as illustrated by the dotted line 22. As a result of the rotation of the X-ray source 3 and the opposite position 15, the X-ray filter 21 is moved to an opposite position 23, so that the overlap region 18 of the opposite second fan beam 17 is attenuated. In the present case, the X-ray filter 21, which may be made of copper, for example, has a cuboid shape, so that the X-ray dose in the overlap region 18 of the first fan beam 14 is attenuated by 50% and the opposite second fan beam 17 inside the overlap region 18 is accordingly also attenuated by 50% done. In total, therefore, a homogeneous X-ray dose of 100% is achieved inside the overlap region 18. To produce the fan beam 14, an aperture 24 is disposed in a fixed position relative to the X-ray source 3, whereby the aperture 24 can be made of tungsten or lead. Upon rotation of the X-ray source 3, the aperture 24 is also moved to an opposite position 25 to produce the second opposite fan beam 17.

Figure 2:
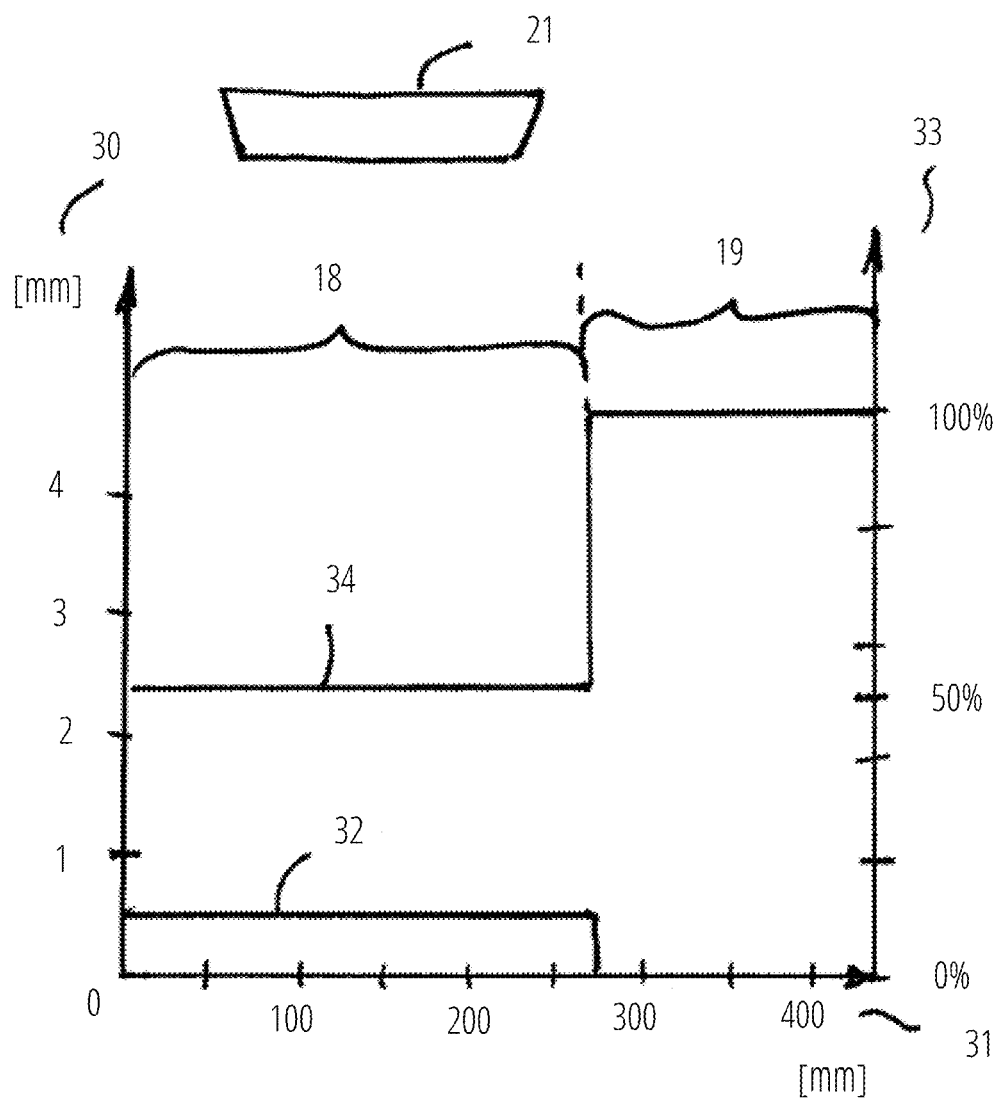

FIG. 2 shows a diagram of a width 30 of the X-ray filter 21 along the central axis 12 of FIG. 1 as a function of a length 31 of the X-ray detector 2 in the direction of movement 5 of FIG. 1. The progression of the width 30 of the X-ray filter 21 as a projection onto the X-ray detector 2, i.e. in dependence of the length of the X-ray detector, is plotted in the first function 32. In the present case, the average energy of the photons of the X-rays of the fan beam 14 is 60 keV. The X-ray filter is made of copper. It can therefore be seen from the first function 32 that the width of the X-ray filter 21 is a constant 0.5 mm inside the overlap region 18, whereby no X-ray filter is disposed inside the first remaining region 19. A transmission 33 between 0% and 100% is plotted on a second, y-axis. A transmission curve 34 thus shows the dependence of the transmission on the length coordinate 31 of the X-ray detector 2, whereby an attenuation of 50% takes place inside the overlap region or, more specifically, the transmission is 50% and the transmission in the first remaining region 19 is 100%.

Figure 3:
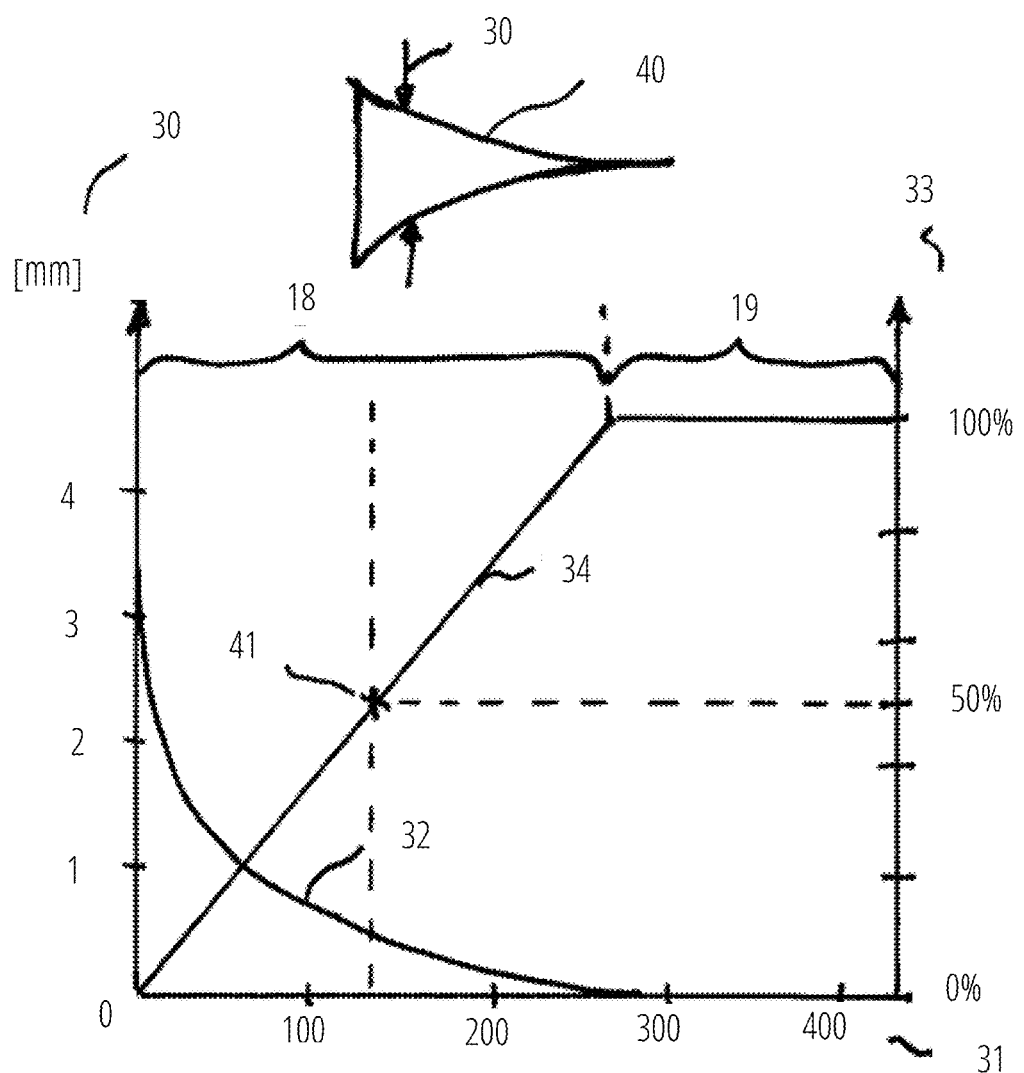

FIG. 3 shows a diagram as in FIG. 2, wherein the function 32 of the width 30 drops sharply in dependence on the length coordinate 31 of the X-ray detector 2. The X-ray filter consequently has a wedge shape 40. The transmission curve 34 therefore increases linearly inside the overlap region 18 from 0% to 100% and remains constant within the remaining region 19 at 100%. The transmission at a center point 41 of the overlap region 18 is 50%. The linearly increasing function 34 is therefore point-symmetrical inside the overlap region 18 relative to the center point of the overlap region 41, so that the addition of the dose of the first fan beam 14 and the dose of the second fan beam 17 of FIG. 1 results in a homogeneous dose distribution of 100%.

Figure 4:
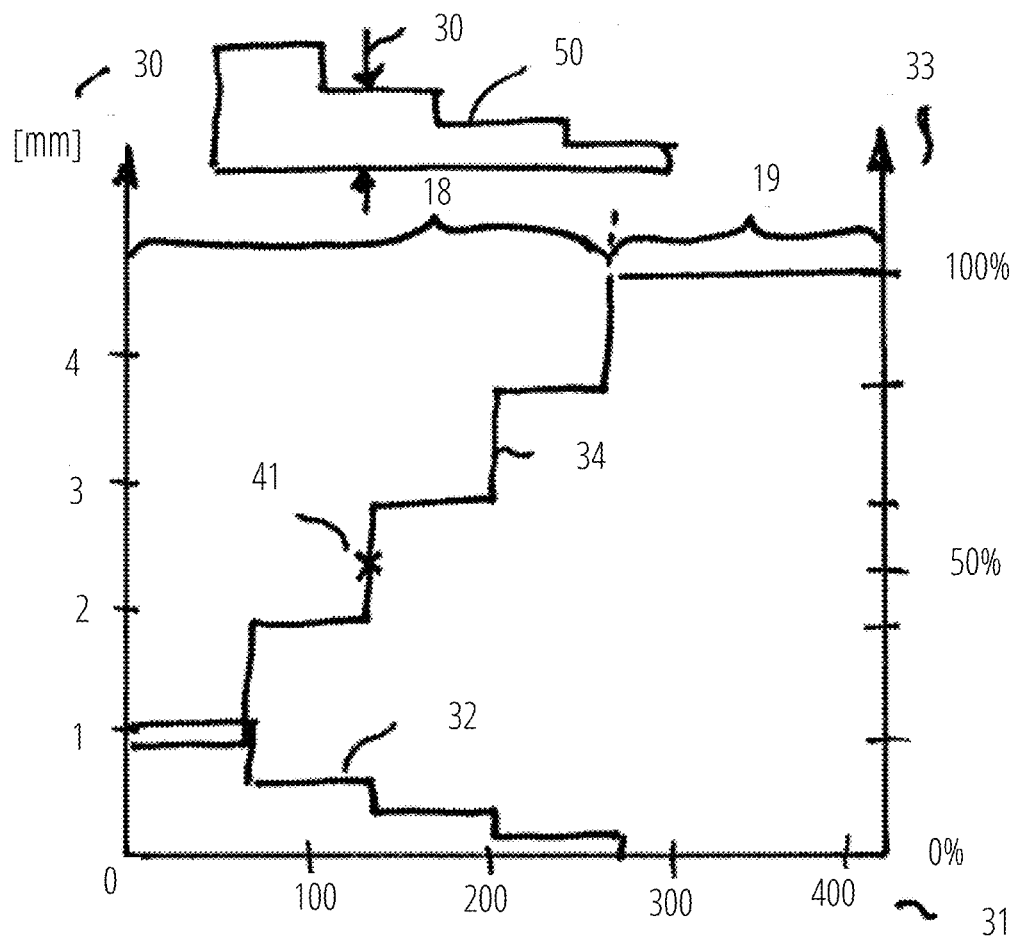

FIG. 4 shows a further embodiment of the X-ray filter, which has a stepped shape 50 with a varying width 30, whereby the associated diagram shows a stepped function 32 of the width 30 in dependence on the length coordinate of the X-ray detector 2. The transmission curve 34 consequently shows a stepped increase inside the overlap region 18, which is point-symmetrical relative to the center point 41 of the overlap region 18. The transmission in the remaining region 19 is 100%. The transmission at the center point 41 of the overlap region is consequently 50%.

Figure 5:
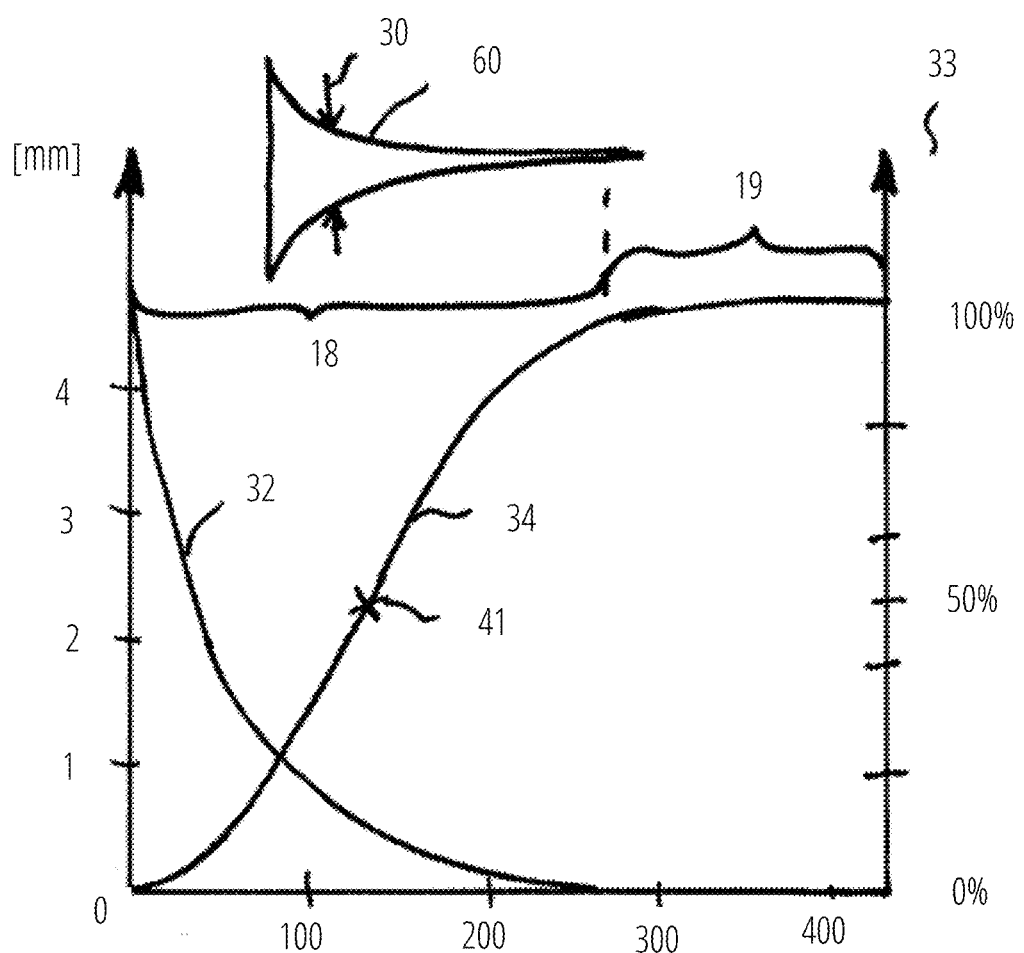

FIG. 5 shows a further embodiment of the X-ray filter having a second wedge shape 60, whereby the width 30 decreases more than for the X-ray filter of FIG. 3. The progression of the function 32 of the width 30 in dependence on the length coordinate 31 thus results in an increasing transmission curve 34, which is point-symmetrical inside the overlap region 18 relative to the center point 41 of the overlap region. The transmission at the center point 41 of the overlap region 18 is 50%. The transmission inside the remaining region 19 stays at 100%.

Figure 6:
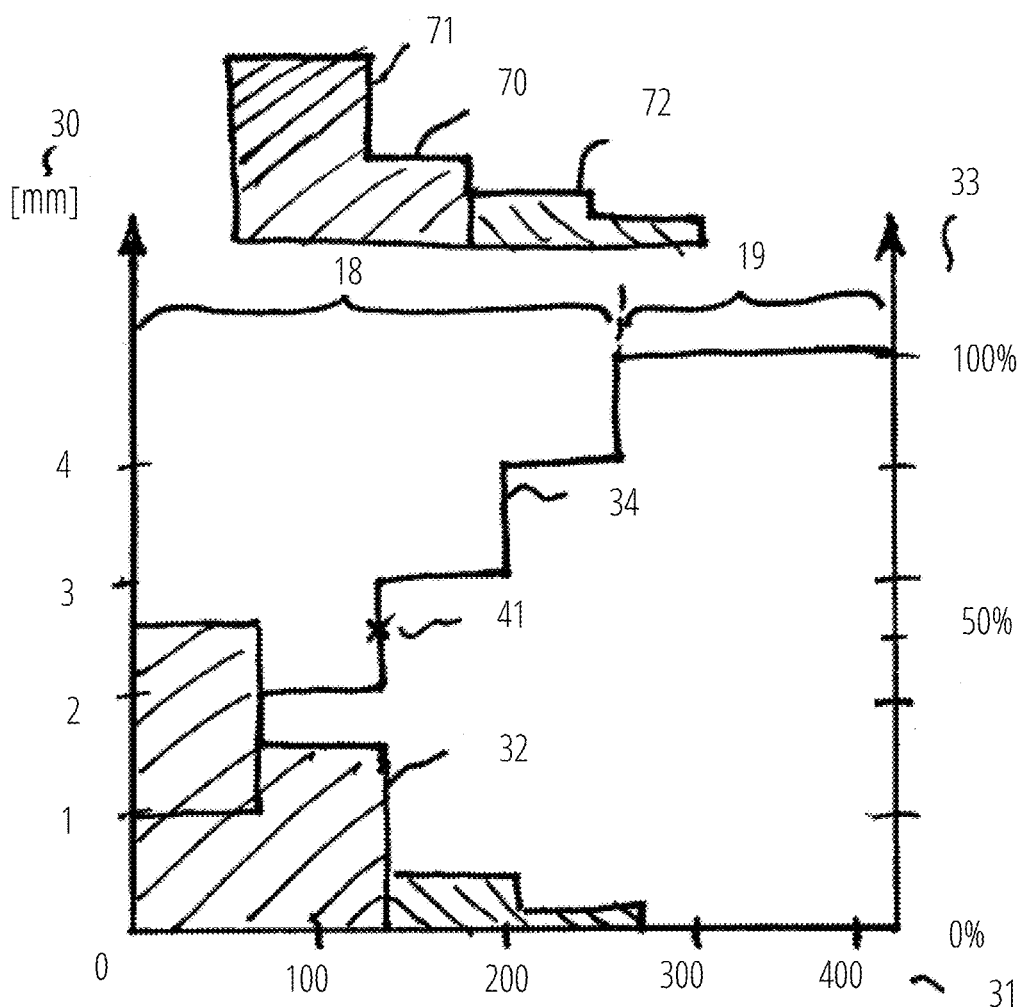

FIG. 6 shows a further embodiment of the X-ray filter 70, comprising a first part 71 and a second part 72, whereby the first part 71 is made of aluminum, for example, and the second part 72 is made of copper, for example. The different X-ray absorption properties of the two parts 71 and 72 and the selected function 32 of the width 30 in dependence of the adjacent coordinate 31, result in the desired stepped transmission curve 34, which extends point-symmetrically inside the overlap region 18 relative to the center point 41 of the overlap region 18. The transmission 33 at the center point 41 is 50%.

Figure 7:
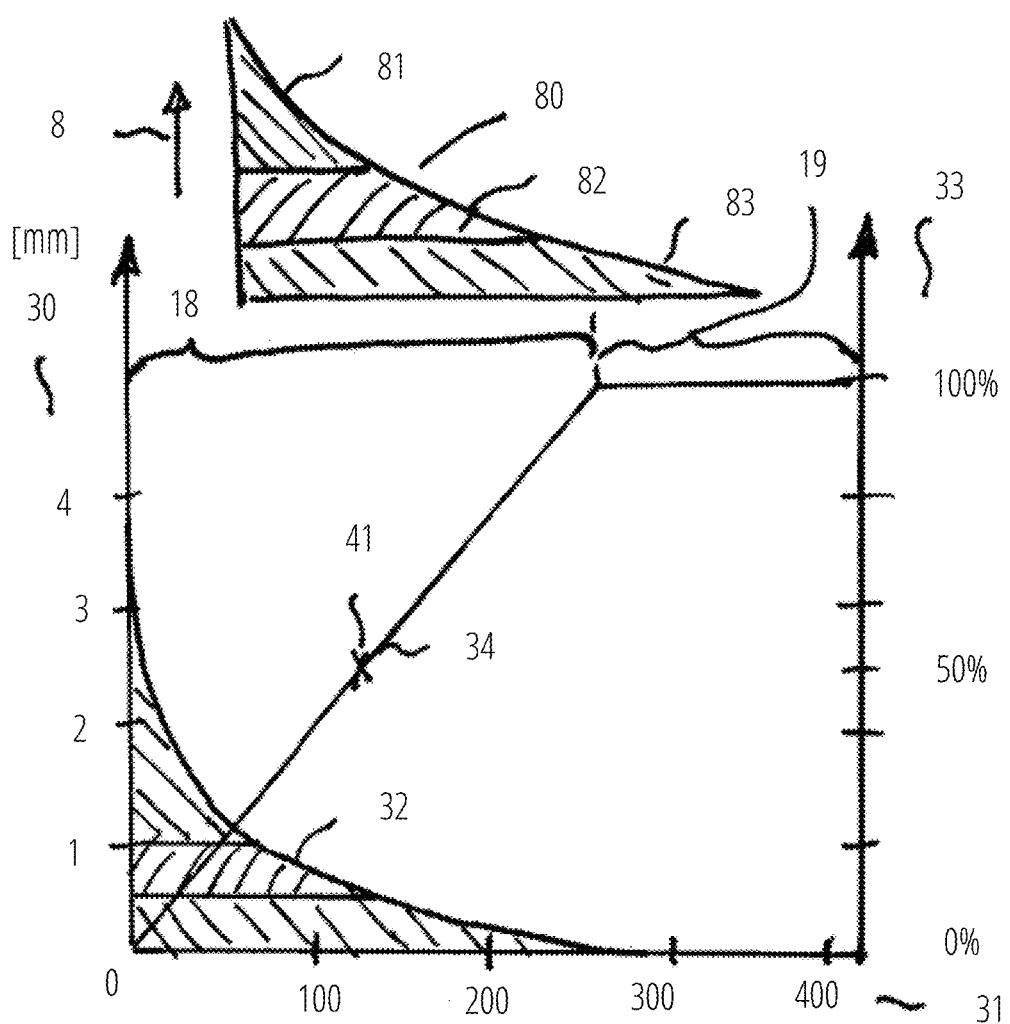

FIG. 7 shows a further embodiment of an X-ray filter 80, comprising a first part 81, a second part 82 and a third part 83, whereby the individual parts 81, 82 and 83 are disposed one above the other in irradiation direction 8. The parts 81, 82 and 83 can be made of different materials. The function 32 of the width 30 in dependence on the length coordinate 31 and the individual materials are therefore selected such that the desired linear progression of the transmission curve 34 inside the overlap region 18 is achieved. The transmission 33 at the center point 41 of the overlap region 18 is 50%.

REFERENCE SIGNS 1 3D X-ray device
2 X-ray detector
3 X-ray source
4 Computer
5 Movement path
6 Object volume
7 Second movement path
8 Irradiation direction
9 X-rays
10 3D X-ray image
11 Patient
12 Central axis
13 Center of rotation
14 First fan beam
15 Opposite position of the X-ray source 3
16 Opposite position of the X-ray detector 2
17 Second, opposite fan beam
18 Overlap region
19 First remaining region
20 Second remaining region
21 X-ray filter
22 Dotted line
23 Opposite position of the X-ray filter
24 Aperture
25 Opposite position of the X-ray source
30 Width of the X-ray filter
31 Length of the X-ray detector
32 First function
33 Transmission
34 Transmission curve
40 Wedge-shaped X-ray filter
41 Center point of the overlap region
50 Stepped X-ray filter
60 Second wedge-shaped X-ray filter
70 Further X-ray filter, two-part
71 First part of the X-ray filter
72 Second part of the X-ray filter
80 Further X-ray filter, three-part
81 First part of the X-ray filter
82 Second part of the X-ray filter
83 Third part of the X-ray filter

The invention claimed is:

1. A 3D X-ray device comprising:
an X-ray detector;
an X-ray source; and
a computer,
wherein the X-ray detector and the X-ray source are configured to be moved about an object volume to be recorded in a craniomaxillofacial region on movement paths with a rotation of at least 185°,
wherein the computer is configured to record a plurality of X-ray projection images from different irradiation directions, with X-rays, which are produced by of the X-ray source,
the device comprising an aperture configured to form a fan beam to irradiate the object volume in one of the irradiation directions, and configured to be captured by the X-ray detector,
wherein the computer is configured to generate a 3D X-ray image of the object volume from the recorded X-ray projection images by a reconstruction method,
wherein the X-ray detector is arranged asymmetrically relative to a central axis through a center of rotation of the 3D X-ray device, wherein a first fan beam and an opposite second fan beam corresponding to a 180° of the first fan beam form an overlap region, the device further comprising:
at least one X-ray filter is disposed between the X-ray source and the object volume having a first width for attenuating an X-ray dose inside the overlap region, characterized in that the device further comprises a second X-ray filter having a second width that differs from the first width of the said at least one X-ray filter disposed inside the overlap region and wherein the second x-ray filter is provided in the regions of the two fan beams outside the overlap region.

2. The 3D X-ray device according to claim 1, wherein the 3D X-ray device is a CT device or a DVT device.

3. The 3D X-ray device according to claim 1, wherein the shape of the X-ray filter is selected such that a transmission curve of the X-ray filter decreases or increases monotonically across the overlap region.

4. The 3D X-ray device according to claim 1, wherein the shape of the X-ray filter is selected such that a transmission curve of the X-ray filter relative to the center of rotation is point-symmetrical and exhibits an attenuation of the X-ray dose of 10-75% in a center point of the overlap region.

5. The 3D X-ray device according to claim 1, wherein the shape of the X-ray filter is a cuboid shape, a wedge shape, a stepped shape or a shape adapted to a weighting curve.

6. The 3D X-ray device according to claim 1, wherein the X-ray detector and the X-ray source are moved about an object volume to be recorded on movement paths with a rotation of at least 360°.

7. The 3D X-ray device according to claim 1, wherein a plurality of X-ray filters of different widths and shapes are disposed between the X-ray source and the object volume for attenuating the X-ray dose inside the overlap region.

8. The 3D X-ray device according to claim 1, wherein the X-ray filter is constructed from a plurality of individual layers with materials having different X-ray absorption properties, wherein the individual layers of the X-ray filter are constructed such that a desired transmission curve is produced.

9. The 3D X-ray device according to claim 1, wherein the X-ray filter is disposed between the aperture and the X-ray source or between the aperture and the object volume.

10. The 3D X-ray device according to claim 1, wherein the computer is configured such that the attenuation of the X-ray dose by the at least one X-ray filter is taken into account in the computation of the 3D X-ray image via the reconstruction method.

11. The 3D X-ray device according to claim 1, wherein the X-ray filter is made of copper or aluminum.

12. The 3D X-ray device according to claim 1, wherein the X-ray filter is automatically moved into a desired position relative to the radiation beam by a control unit and a drive unit.

13. A method for producing a 3D X-ray image by the 3D X-ray device according to claim 1, wherein the attenuation of the X-ray dose by the X-ray filter is taken into account in the computation of the 3D X-ray image from the individual X-ray projection images by the reconstruction method.

* * * * *